(12) United States Patent
Kolasa et al.

(10) Patent No.: US 7,549,964 B2
(45) Date of Patent: Jun. 23, 2009

(54) MULTIPLE FREQUENCY DOPPLER ULTRASOUND PROBE

(75) Inventors: William Kolasa, Belleville, WI (US); Ryan W. Jennings, Madison, WI (US); Evan K. Davis, Madison, WI (US)

(73) Assignee: Viasys Healthcare, Inc., Madison, WI (US)

( * ) Notice: Subject to any disclaimer, the term of this patent is extended or adjusted under 35 U.S.C. 154(b) by 256 days.

(21) Appl. No.: 11/418,483

(22) Filed: May 4, 2006

(65) Prior Publication Data

US 2007/0276252 A1 Nov. 29, 2007

(51) Int. Cl.
A61B 8/06 (2006.01)

(52) U.S. Cl. .................... 600/459; 73/625; 73/626; 367/157; 367/180

(58) Field of Classification Search .............. 600/459; 73/609, 625, 628, 632; 367/135, 152, 157, 367/138, 180

See application file for complete search history.

(56) References Cited

U.S. PATENT DOCUMENTS

| | | | |
|---|---|---|---|
| 3,292,018 A | 12/1966 | Clynes | |
| 3,309,914 A | 3/1967 | Weighart | |
| 3,617,993 A | 11/1971 | Massie | |
| 3,924,454 A | 12/1975 | McElroy et al. | |
| 4,357,944 A | 11/1982 | Mauser et al. | |
| 4,459,853 A | 7/1984 | Miwa et al. | |
| 4,534,221 A | 8/1985 | Fife et al. | |
| 4,630,612 A | 12/1986 | Uchida et al. | |
| 4,755,953 A | 7/1988 | Geithman et al. | |
| 4,872,346 A | 10/1989 | Kelly-Fry et al. | |
| 4,963,782 A * | 10/1990 | Bui et al. | 310/358 |
| 5,213,104 A | 5/1993 | Reynolds | |
| 5,379,770 A | 1/1995 | Van Veen | |
| 5,410,205 A | 4/1995 | Gururaja | |
| 6,344,024 B1 | 2/2002 | Brucher et al. | |

FOREIGN PATENT DOCUMENTS

WO WO 2005/006954 A2 7/2004

OTHER PUBLICATIONS

"A Dual Frequency Ultrasonic Probe for Medical Applications: This article outlines using multilayer ceramics to simultaneously obtain B mode and Doppler mode imaging." IEEE Transactions on Ultrasonics, Ferroelectrics, and Frequency Control, vol. 42, No. 2, Mar. 1995.

* cited by examiner

Primary Examiner—Brian Casler
Assistant Examiner—Parikha S Mehta
(74) Attorney, Agent, or Firm—Baker & Hostetler LLP

(57) ABSTRACT

A method of measuring blood flow through a blood vessel is provided using a single quasi-continuous mode probe that can support multiple frequencies without increasing the probe tip size. A plurality of elements are provided in the probe tip. Each element emits ultrasound waves using a long pulsed signal with each element having a different resonant frequency. Each element also receives ultrasound energy in a continuous mode. A selector is manually controlled by a practitioner to select the active element. The output may take a variety of forms. For example, the output may be printed, displayed, recorded to a memory, and/or played through a speaker or headset.

21 Claims, 3 Drawing Sheets

MULTIPLE FREQUENCY DOPPLER ULTRASOUND PROBE

FIELD OF THE INVENTION

The subject of the disclosure relates generally to ultrasound probes. More specifically, the disclosure relates to medical Doppler ultrasound probes that can operate at multiple frequencies.

BACKGROUND

To measure blood flow, a hand held probe is typically used to transmit a beam of ultrasonic energy through body tissue to a target blood vessel. Blood cells flowing through the blood vessel scatter the ultrasonic energy in many directions. A portion of the transmitted ultrasonic energy is reflected back to the probe, which receives and processes the reflected energy. In accordance with the well known Doppler phenomenon, the frequency of the received signal is different than that of the source signal due to the velocity (magnitude and direction) of the blood cells. Movement toward the probe compresses the wavelength of the reflected wave, causing an increase in the frequency. Movement away from the probe lengthens the wavelength of the reflected wave, resulting in a decrease in the frequency. This difference between the emitted and received frequencies is known as the Doppler shift. Thus, the speed and direction of blood flow within a blood vessel can be measured in a noninvasive manner using ultrasound emissions and the measured shift in frequency of the received signal. Similarly, a heartbeat, such as a fetal heartbeat, can be measured using ultrasound emissions.

With a continuous-wave (CW) Doppler ultrasound probe, a piezoelectric crystal or element contained inside the probe tip continuously transmits an ultrasonic beam that is reflected by the circulating red blood cells. A separate crystal in the tip continuously receives the reflected sound waves. The transmit and receive crystals are often made from a circular element that has been cut down the middle into two semi-circle shaped elements. The two semi-circles are fixed side by side inside the probe tip with a slight angle to each other to form an intersection of the beam patterns in a patient. Alternate arrangements include using two side-by-side square crystals or a central disk surrounded by an annular ring element. Processing is done on the received signal to extract the Doppler shift frequency. Simplicity of design, ease of use, and low power consumption make CW Doppler the typical choice for small battery powered applications. Also, sensitivity of CW Doppler is typically high because damping of the crystals is not required as known to those skilled in the art The useful operating frequency range for Doppler ultrasound probes is typically 2-10 megahertz (MHz). The required depth of penetration in body tissue determines the operating frequency based on well-known attenuation effects as a function of frequency. A lower probe frequency provides deeper penetration of the body tissue. Thus, in the medical field, probes having frequencies from about 2 to about 3 MHz may be used to detect deep blood flow, fetal blood flow, or intracranial blood flow due to their deeper penetration of body tissue. Probes having frequencies from about 4 to about 5 MHz may be used to detect vascular blood flow, for example, in the neck, arms, or legs. Probes having frequencies from about 8 to about 10 MHz may be used to detect blood flow in vessels near the skin or in intraoperative applications.

The transmitting piezoelectric crystal is electrically stimulated to produce an ultrasound signal at a specific frequency, for example 2, 3, 4, 5, 8, etc. MHz. The crystal has geometrical and material characteristics that define a specific resonant frequency. CW crystals are typically used undamped with a narrow bandwidth and high Q factor. Operating the undamped crystal at its resonant frequency creates the most efficient ultrasound transmitter and requires the lowest energy power source. Conversely, an undamped receiving crystal is most efficient at producing a voltage when deformed by pressure at or near its resonant frequency. An efficient receive crystal reduces ultrasound exposure risks by allowing lower ultrasound energy to be transmitted into tissue. To change the operating frequency during use, for example from 2 to 3 MHz or from 5 to 8 MHz, a CW ultrasound probe is typically replaced with a probe designed for the desired frequency. Alternatively, the probe can be designed with damped or backed crystals to provide a wider bandwidth of operation and multiple frequencies, but with reduced efficiency due to the wider bandwidth. Additional crystals can be mounted in the probe. For example, two 5 MHZ and two 8 MHz crystals can be mounted in the probe tip. However, the resulting increase in the size of the probe tip make it potentially awkward for a practitioner to use. Thus, a practitioner must carry and manually switch between multiple probes, accept use of a probe having a reduced sensitivity and high transmit power, or use a bulky probe including multiple crystals to provide blood flow measurements at multiple frequencies. What is needed therefore is a system that provides multiple frequencies selectable for optimal signal acquisition in a single probe without reduced sensitivity or loss of Doppler signal. What is further needed is a system that provides the multiple frequencies with little or no increase in the size of the probe tip.

SUMMARY

An exemplary embodiment of the present invention provides a single Doppler ultrasound probe that can operate at multiple frequencies for measuring blood flow without increasing the probe tip size above that of a single frequency CW probe. Multiple elements of differing resonant frequencies are provided in the probe tip. In an exemplary embodiment, each element is a piezoelectric crystal. Each element can transmit ultrasound waves using a pulsed signal and receive ultrasound waves continuously. A switch is manually controlled by a practitioner to select the optimum probe frequency dependent on the application. The Doppler shift output may be presented to the user in a variety of forms. For example, the output may be printed, displayed, recorded to a memory, and/or played through a speaker or headset. The manual selector is operatively connectable to a plurality of elements.

A method of determining blood flow velocity through a blood vessel or a heart rate is provided. Using a selector, a practitioner manually selects an element to provide a measured output. The method includes, but is not limited to, receiving a frequency selection from a manual selector, wherein the frequency selection identifies an element from a plurality of elements; generating a pulsed transmit signal; emitting energy from the identified element toward an object in response to the generated pulsed signal; receiving a reflected signal from the object at the identified element; processing the received signal to determine a characteristic of the object; and outputting the characteristic of the object. For example, the object may be a blood vessel and the characteristic may be a blood flow velocity or a heart rate.

Another exemplary embodiment of the invention includes an ultrasound probe capable of implementing the operations of the method and including a plurality of elements. Another exemplary embodiment of the invention includes an ultrasound system including the ultrasound probe.

Other principal features and advantages of the invention will become apparent to those skilled in the art upon review of the following drawings, the detailed description, and the appended claims.

BRIEF DESCRIPTION OF THE DRAWINGS

Exemplary embodiments of the invention will hereafter be described with reference to the accompanying drawings, wherein like numerals will denote like elements.

DETAILED DESCRIPTION

Ultrasound refers to the use of ultrasonic waves or waves with a frequency over 20 kilohertz (kHz). For use in Doppler medical devices, sound waves are transmitted through body tissues using a probe. The probe is placed directly on top of the skin, which generally has a coupling gel applied to the surface. The sound waves are reflected by different body tissue and blood as "echoes." Portions of the echoes return to the probe and are processed to determine the Doppler shift frequencies. The results are sent to an output media.

Figure 1:
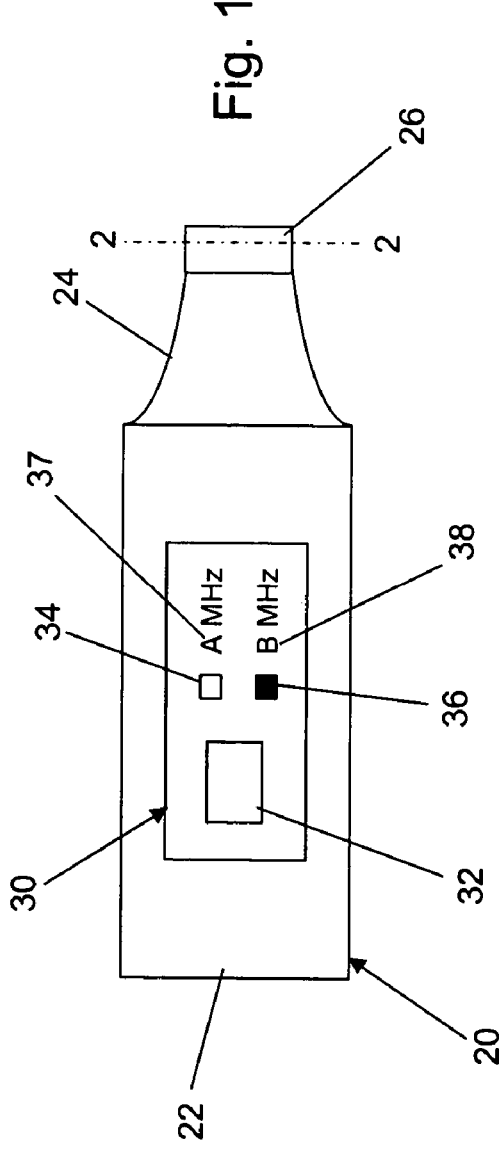
FIG. 1 is an external side view of an ultrasound probe including a manual switch for selecting a frequency of operation in accordance with an exemplary embodiment.

With reference to FIG. 1, a side view of an ultrasound probe 20 having a manually selectable operating frequency in accordance with the invention is shown. Ultrasound probe 20 may include a housing 22, a probe neck 24, and a probe tip 26. Housing 22 houses the electronics for operating ultrasound probe 20 and is held in the hand of a practitioner. Housing 22 may have a different size and shape to accommodate different applications and may vary depending on the size and arrangement of the electronics. Probe neck 24 connects housing 22 to probe tip 26 and has a generally tapered exterior surface. The size and shape of probe neck 24 may vary depending on the relative size and shape between housing 22 and probe tip 26. Probe tip 26 houses a plurality of elements that each emit and receive pulsed energy at different ultrasound frequencies. In an exemplary embodiment, each element is a piezoelectric crystal. Probe neck 24 houses electrical wires that connect the elements in probe tip 26 to the electronics in housing 22. Different and additional components may be included with ultrasound probe 20. For example, ultrasound probe 20 may include one or more power source, various connectors, a display, a printer, a speaker, etc. Alternatively, ultrasound probe 20 may connect with a separate device that houses the additional components and optionally the electronics.

Housing 22 includes a frequency selection interface 30. Frequency selection interface 30 may be mounted on any side of housing 22 and may include a manual switch 32, a first indicator 34, and a second indicator 36. Manual switch 32 may be any type of switch as known to those skilled in the art both now and in the future. Manual switch 32 provides a mechanism by which the practitioner selects an operating frequency (or active element) of an ultrasound probe 20. In an exemplary embodiment, first indicator 34 is a light emitting diode (LED) that is "on" when the switch selects the element indicated by a first frequency 37. In an exemplary embodiment, second indicator 36 is a light emitting diode (LED) that is "on" when the switch selects the element indicated by a second frequency 38. As known to those skilled in the art both now and in the future, other methods for indicating a frequency selection may be implemented with ultrasound probe 20. Manual switch 32 and the indicators provide a means for a practitioner to select from a plurality of elements having unique resonant frequencies. Additional manual selectors are possible including those that allow selection from among three or more elements. For example, to select from three or more elements, a dial or a sliding switch may be used as a manual selector. Frequency selection interface 30 may also be located on a separate device connected to the probe.

Figure 3:
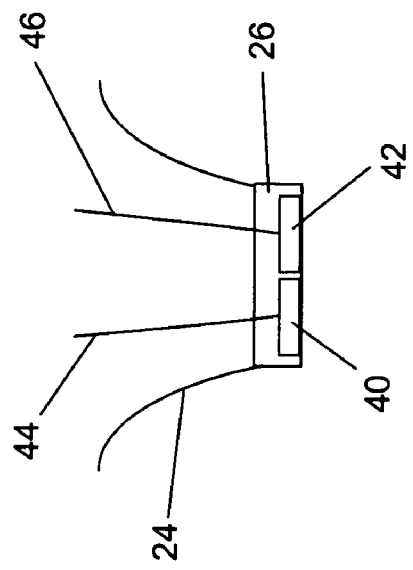
FIG. 3 is a second cross sectional view of the tip of the ultrasound probe of FIG. 2.
Figure 2:
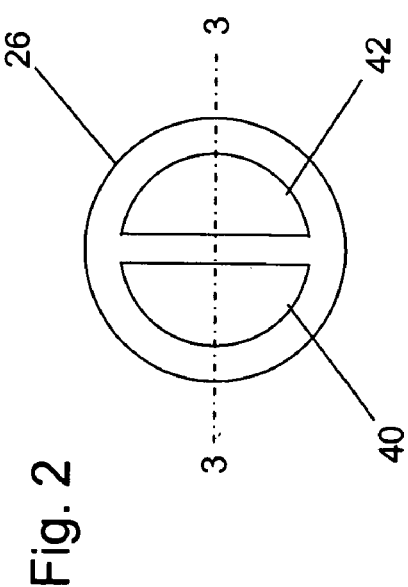
FIG. 2 is a first cross sectional view of the tip of the ultrasound probe of FIG. 1.

With reference to FIG. 2, a cross sectional view of probe tip 26 is shown along axis 2-2 of FIG. 1. Probe tip 26 includes a first element 40 and a second element 42 mounted adjacent each other. Probe tip 26 may also include additional elements. First element 40 and second element 42 are shaped in a semi-circle. Alternative shapes are possible with the effect of changing the distribution of energy emitted by the element. With reference to FIG. 3, a cross sectional view of probe tip 26 is shown along 3-3 of FIG. 2. First electrical wires 44 connect first element 40 with the electronics housed in housing 22. Second electrical wires 46 connect second element 42 with the electronics housed in housing 22.

First element 40 and second element 42 contain a piezoelectric material to generate the ultrasound pulses. First element 40 and second element 42 are used both for generating the ultrasound pulses and for receiving the echoes that result from energy reflected back to the element from the target object. When the piezoelectric material is subjected to an electrical voltage, it undergoes a change in dimension depending on the polarity of the voltage. Alternating voltage near the resonant frequency of the element produces ultrasound pressure waves. Conversely, when a reflected pressure wave strikes the piezoelectric material, it causes mechanical deformation of the piezoelectric material which produces an electrical voltage. Piezoelectric materials include natural and synthetic materials such as quartz, ceramics, polymers, etc. Piezoelectric materials can be manufactured in many different shapes and sizes.

Piezoelectric materials typically resonate within narrowly defined frequency ranges. Operating the element undamped at or near the resonant frequency is most efficient, and thus, requires the lowest operating power. First element 40 and second element 42 have distinct resonant frequencies selected by the practitioner based on the clinical need. First element 40 and second element 42 may combine any pair of resonant frequencies over the ultrasound spectrum. In an exemplary embodiment, the ultrasound spectrum utilized extends from about two megahertz (MHz) to about ten MHz. In a first exemplary embodiment, first element 40 has a resonant frequency of about five MHz while second element 42 has a resonant frequency of about eight MHz. In a second exemplary embodiment, first element 40 has a resonant frequency of about two MHz while second element 42 has a resonant frequency of about three MHz. The resonant frequencies may be varied depending on the particular embodiment. For example, instead of two MHz, the resonant frequency may be about 2.25 MHz.

In order to use the same element for both transmission and reception of ultrasound energy, a quasi-continuous or long pulse mode of operation is used. The transmit signal is gated on and off at a 50% duty cycle. For simplicity of operation and design, the receive signal is not gated, and thus, return energy from all tissue depths is processed. The pulse repetition frequency (PRF) of the transmit signal is determined by the required operating depth. Because the same element both emits and receives the energy, the transmission time must be coordinated based on the expected depth of the target object (and resulting delay time before the reflection returns back to the element) resulting in a range of possible pulse repetition rate or frequencies (PRFs) based on the frequency selected. Using a frequency range from about two MHz to about ten MHz, an exemplary PRF range extends from about five kHz to about 125 kHz. Using a frequency range from about five MHz to about eight MHz, an exemplary PRF range extends from about 62 kHz to about 63 kHz. Preferably, using a frequency range from about five MHz to about eight MHz, the PRF is 62.5 kHz. Using a frequency range from about two MHz to about three MHz, an exemplary PRF range extends from about five kHz to about six kHz. Preferably, using a frequency range from about two MHz to about three MHz, the PRF is 5.3 kHz.

In alternative embodiments, probe tip 26 may include a lens mounted in front of first element 40 and/or second element 42 to focus or to defocus the energy emitted from either element. For example, a lens formed of plastic material may be arranged in front of first element 40 and/or second element 42 to narrow the beam of emitted energy to assist in locating a target blood vessel. Additionally, probe tip 26 may use a single or multilayered waveplate in front of first element 40 and second element 42 to reduce the acoustic impedance mismatch at the probe/tissue interface. In use, first element 40 and second element 42 emit through a coupling medium such as a gel that is placed on the surface of the medium to be analyzed. For example, a gel is placed on the skin of a patient, and the probe tip 26 is placed on top of the gel.

Figure 4:
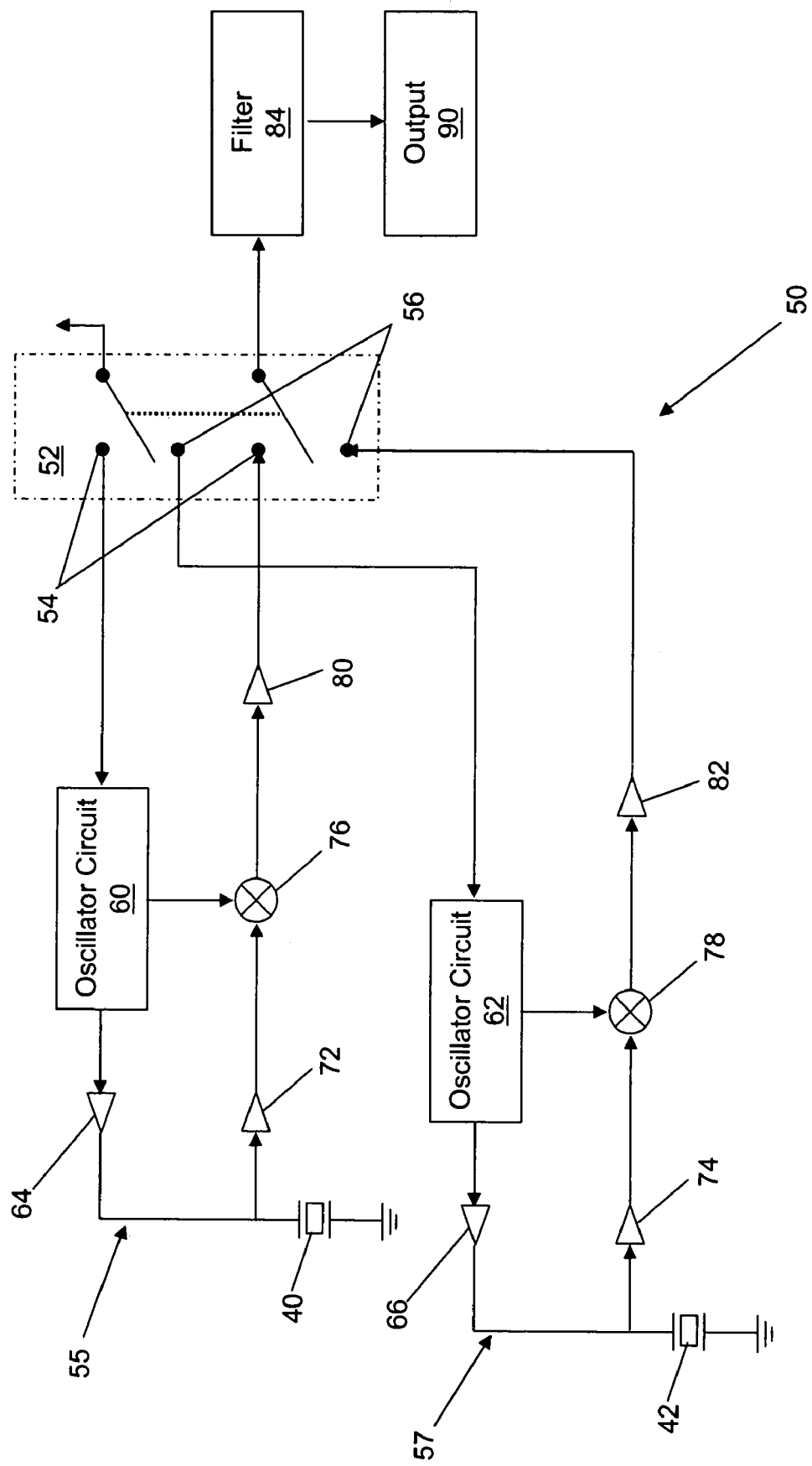
FIG. 4 is a component diagram of the probe circuit in accordance with an exemplary embodiment.

With reference to FIG. 4, electronics 50 in accordance with an exemplary embodiment are shown. Electronics 50 include electronic switch 52, a first element circuit 55, a second element circuit 57, a filter 84, and an output 90. Setting of electronic switch 52 between a first position 54 and a second position 56 is controlled by manual switch 32. First position 54 selects first element circuit 55. Second position 56 selects second element circuit 57. In the exemplary embodiment of FIG. 4, electronic switch 52 activates only one of first element circuit 55 or second element circuit 57 disabling the other circuit 55, 57. First element circuit 55 may include a first oscillator circuit 60, a first transmit amplifier 64, first element 40, a first receive circuit 72, a first mixer 76, and a first amplifier 80. Second element circuit 57 may include a second oscillator circuit 62, a second transmit amplifier 66, second element 42, a second receive circuit 74, a second mixer 78, and a second amplifier 82.

First oscillator circuit 60 and second oscillator circuit 62 produce a series of pulses at a pre-selected PRF and center frequency. The center frequency is approximately equal to the resonant frequency of the respective elements 40, 42. First transmit amplifier 64 and second transmit amplifier 66 amplify the high frequency oscillation output of first oscillator circuit 60 and second oscillator circuit 62, respectively, and provide a high frequency voltage to first element 40 and second element 42, respectively, while providing high impedance during receive. The high frequency voltage is converted to ultrasound emitted by first element 40 or second element 42 toward an object of interest. For example, the ultrasound energy is emitted toward a blood vessel or a heart.

A portion of the reflected ultrasound is received by first element 40 or second element 42 and is converted into electronic signals received at first receive circuit 72 and second receive circuit 74, respectively. First receive circuit 72 and second receive circuit 74 provide electrical matching, limiting, and signal gain. The Doppler shift of the reflected signal is detected using first mixer 76 and/or second mixer 78. In first mixer 76 and second mixer 78, the respective received signal is electronically mixed with the high frequency input signal of first oscillator circuit 60 and second oscillator circuit 62, respectively. By mixing the two sound waves, four frequency components are obtained: 1) the frequency of the transmitted signal, 2) the frequency of the reflected signal, 3) the frequency of the sum of the two signals, and 4) the frequency of the difference between the two signals. The difference signal includes the Doppler shift frequency that is proportional to the relative velocity of the target object. In the exemplary embodiment of FIG. 4, electronic switch 52 selects either first mixer 76 or second mixer 78 to minimize noise from the unused element circuit. First amplifier 80 and second amplifier 82 buffer and scale the mixer output as required. Filter 84 may include a low pass filter to remove higher frequency components created as a result of the pulsed mode of operation and a high pass filter to remove low frequency noise and low frequency Doppler components. In alternative embodiment, a bandpass filter may be used. Output 90 receives the filtered difference signal.

Figure 5:
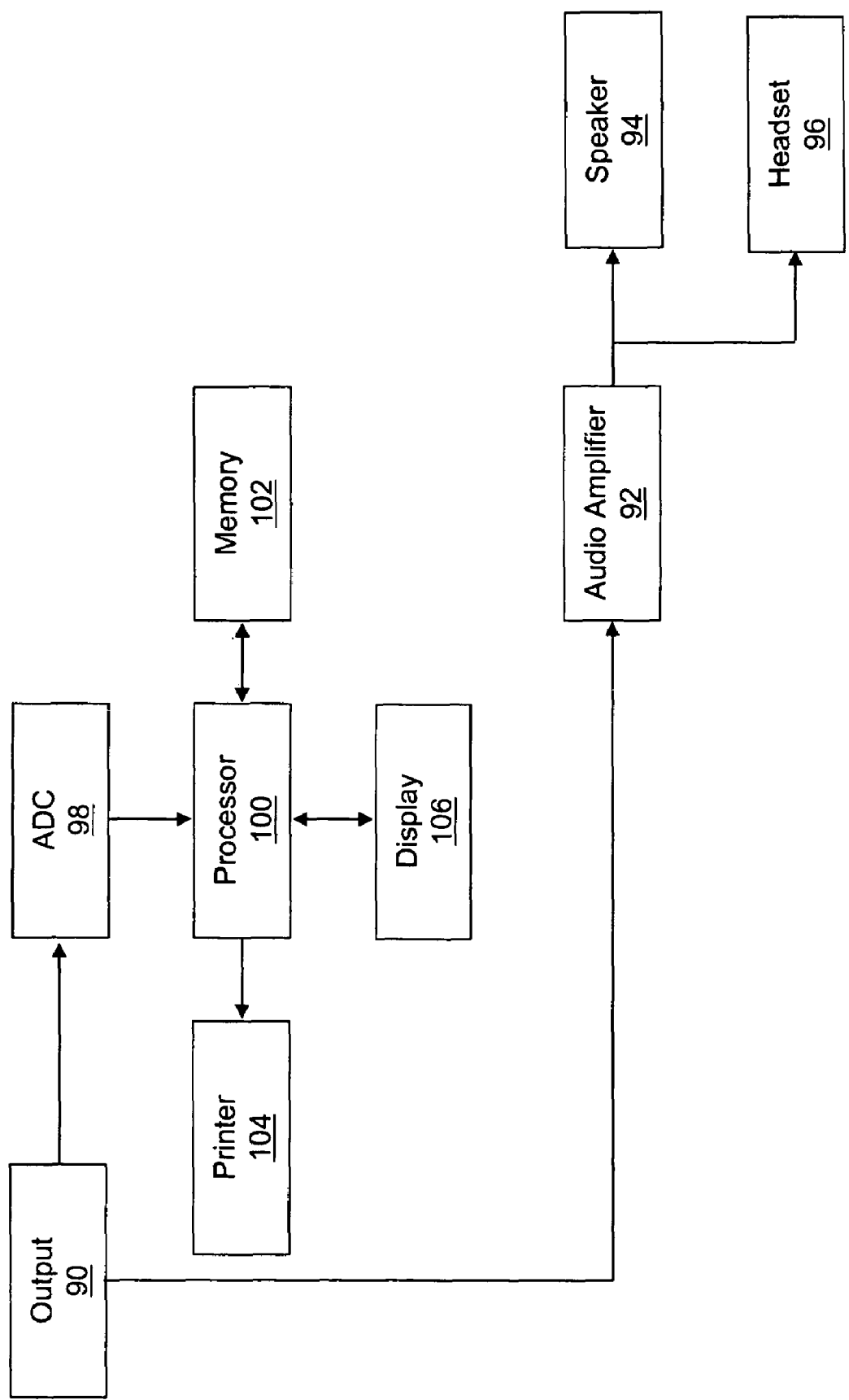
FIG. 5 is a block diagram depicting structure and operations performed in the processing of the output of the probe circuit of FIG. 4.

With reference to FIG. 5, the filtered signal may be output from ultrasound probe 20 in a variety of forms. Some or all of the various forms may be implemented within housing 22 of ultrasound probe 20. Alternatively, ultrasound probe 20 may connect to a separate device that includes some or all of the various forms of output media. For example, ultrasound probe 20 may connect using various wired or wireless media to a separate device. Output structures include, but are not limited to, a speaker 94, a headset 96, a printer 104, a display 106, and a memory 102. The output signal may be fed to an audio amplifier 92 that provides its output to speaker 94 and/or headset 96. Simultaneously, the output filtered signal may be provided to analog-to-digital converter (ADC) 98 which provides digital output data to a processor 100, which performs real time buffering and signal processing, manages communications with the user, and executes instructions.

Processor 100 executes instructions that may be written using one or more programming language, scripting language, assembly language, etc. The instructions may be carried out by a special purpose computer, logic circuits, or hardware circuits. Thus, processor 100 may be implemented in hardware, firmware, software, or any combination of these methods. The term "execution" is the process of running an application or the carrying out of the operation called for by an instruction. The output data from processor 100 can be provided to printer 104, display 106, and/or memory 102. The information displayed on display 106, recorded on printer 104, and stored in memory 102 can take various forms as known to those skilled in the art both now and in the future.

For example, because not all blood cells in the sample volume are moving at the same speed, a range or spectrum of Doppler shifted frequencies are reflected back to ultrasound probe 20. Thus, the signal received at ultrasound probe 20 may be processed to produce a velocity profile of the blood flow, which varies over the period of a heartbeat to produce a beat-to-beat flow pattern on a display. Color coding may be used to indicate the proportion of blood cells flowing within that particular velocity range. The information displayed on the video screen can be used by a trained observer to determine blood flow characteristics at particular positions within the blood vessel of the individual being tested, and can detect anomalies in such blood flow, for example, the possible presence of a blockage or restriction, or the passage of an embolus through the artery.

As known to those skilled in the art, electronic switch 52 may be located at a different position within element electronics 50. For example, both element circuits 55, 57 may transmit and receive simultaneously, and electronic switch 52 may select which element circuit drives output 90. Using this alternative embodiment, each element circuit includes a separate filter 84 and only switches the output line connecting to output 90.

The foregoing description of exemplary embodiments of the invention have been presented for purposes of illustration and of description. It is not intended to be exhaustive or to limit the invention to the precise form disclosed. Modifications and variations are possible in light of the above teachings or may be acquired from practice of the invention. Additional circuits and/or instructions may be added to improve the signal quality, integrated chips may be used to perform multiple or all functions together, etc. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. An ultrasound probe, comprising:
a first element circuit, including a first element that emits a first transmit signal toward an object and receives a first reflected signal from the object, the first transmit signal including a first center frequency and a first pulse repetition frequency; and
a second element circuit, including a second element that emits a second transmit signal toward the object and receives a second reflected signal from the object, the second transmit signal including a second center frequency and a second pulse repetition frequency; and
a switch, coupled to the first and second element circuits, to selectively activate and deactivate the first and second element circuits and to operatively couple the activated element circuit to an output, the switch including a first position that activates the first element circuit and deactivates the second element circuit, and a second position that deactivates the first element circuit and activates the second element circuit.

2. The ultrasound probe of claim 1 wherein the first center frequency is in the range from about 2 megahertz (MHz) to about 10 MHz.

3. The ultrasound probe of claim 1 wherein the first center frequency is about 2 megahertz (MHz) and the second center frequency is about 3 MHz.

4. The ultrasound probe of claim 3 wherein the second pulse repetition frequency is in the range from about 5 kilohertz (kHz) to about 6 kHz.

5. The ultrasound probe of claim 4 wherein the first pulse repetition frequency is about 5.3 kHz.

6. The ultrasound probe of claim 1 wherein the first center frequency is about 5 megahertz (MHz) and the second center frequency is about 8 MHz.

7. The ultrasound probe of claim 6 wherein the second pulse repetition frequency is in the range from about 62 kilohertz (kHz) to about 63 kHz.

8. The ultrasound probe of claim 7 wherein the first pulse repetition frequency is about 62.5 kHz.

9. The ultrasound probe of claim 1, wherein the first element and the second element are piezoelectric crystals.

10. The ultrasound probe of claim 9 wherein a shape of the piezoelectric crystals is selected from the group consisting of a semicircular shape and a rectangular shape.

11. The ultrasound probe of claim 9 further comprising a tip, wherein the first element and the second element are mounted adjacent to each other in the tip.

12. The ultrasound probe of claim 11 wherein the first element and the second element are mounted without a backing material.

13. The ultrasound probe of claim 1, wherein the second center frequency is different than the first center frequency.

14. A method of determining a characteristic of an object, the method comprising:
selecting one of a plurality of switch positions including a first switch position that activates a first element circuit and deactivates a second element circuit, and a second switch position that deactivates the first element circuit and activates the second element circuit;
generating, by the activated element circuit, a pulsed signal;
emitting, from the activated element circuit, energy toward an object;
receiving, by the activated element circuit, a reflected signal from the object;
processing the received signal to determine a characteristic of the object; and
outputting the characteristic of the object.

15. The method of claim 14 wherein the object is a blood vessel and the characteristic of the blood vessel is a blood flow velocity.

16. The method of claim 14 wherein receiving the reflected signal is continuous.

17. An ultrasound system, comprising:
a first element circuit, including an oscillator, a transmit amplifier, a piezoelectric element, a receive circuit, a mixer and a receive amplifier, that generates a first transmit signal including a first center frequency and a first pulse repetition frequency;
a second element circuit, including an oscillator, a transmit amplifier, a piezoelectric element, a receive circuit, a mixer and a receive amplifier, that generates a second transmit signal including a second center frequency and a second pulse repetition frequency; and
a switch, coupled to the first and second element circuits, to selectively activate and deactivate the first and second element circuits and to operatively couple the activated element circuit to an output, the switch including a first position that activates the first element circuit and deactivates the second element circuit, and a second position that deactivates the first element circuit and activates the second element circuit.

18. The ultrasound system of claim 17 wherein the output is selected from the group consisting of a display, a printer, a speaker, an audio headset, and a memory.

19. The ultrasound system of claim 17 wherein the first element circuit generates the first transmit signal only if the switch activates the first circuit.

20. The ultrasound system of claim 17 wherein the second element circuit transmits the second transmit signal only if the switch activates the second element circuit.

21. The ultrasound system of claim 17, wherein the second center frequency is different than the first center frequency.

* * * * *